United States Patent [19]
Mainz et al.

[11] Patent Number: 5,984,993
[45] Date of Patent: Nov. 16, 1999

[54] METHOD AND COMPOSITION FOR ODOR CONTROL

[75] Inventors: Eric L. Mainz, Colwich; David B. Griffith, Wichita, both of Kans.

[73] Assignee: Vulcan Materials Company, Wichita, Kans.

[21] Appl. No.: 09/044,876

[22] Filed: Mar. 20, 1998

[51] Int. Cl.$^6$ .................. C05F 3/00; C02F 1/72; A61L 11/00; A61L 9/00
[52] U.S. Cl. .................. 71/12; 71/15; 210/916; 210/758; 422/5; 422/28; 252/187.23; 424/76.5; 424/76.6; 424/76.7
[58] Field of Search .................. 210/916, 758; 422/28, 5; 71/11, 12, 15; 424/76.1, 76.21, 76.5, 76.6, 76.7; 252/187.23

[56] References Cited

U.S. PATENT DOCUMENTS

| | | | |
|---|---|---|---|
| 2,711,363 | 6/1955 | Waibel | 23/85 |
| 3,966,450 | 6/1976 | O'Neill et al. | 71/15 |
| 3,967,039 | 6/1976 | Ninane et al. | 428/403 |
| 3,997,462 | 12/1976 | Denaeyer et al. | 252/187 R |
| 4,007,262 | 2/1977 | Bowers | 424/76 |
| 4,108,771 | 8/1978 | Weiss | 210/50 |
| 4,681,687 | 7/1987 | Mouche | 210/764 |
| 4,911,843 | 3/1990 | Hunniford et al. | 210/610 |
| 4,995,987 | 2/1991 | Whitekettle et al. | 210/754 |
| 5,114,587 | 5/1992 | Hagerstedt | 210/614 |
| 5,336,431 | 8/1994 | Richards et al. | 252/184 |
| 5,820,822 | 10/1998 | Kross | 422/37 |

FOREIGN PATENT DOCUMENTS

| 1175851 | 7/1989 | Japan | A61L 9/01 |
|---|---|---|---|

OTHER PUBLICATIONS

A. Jobbagy, et al., "Sewer System Odour Control In The Lake Balaton Area", *Wat. Sci. Tech.*, vol. 30, No. 1, pp. 195–204, 1994.

CA 122:196088, "Deodorization of Sludge for dewatering by controlled adding chlorite", Hina, Seiya (Kurita Water Ind Ltd., Japan) Jpn. Kokai Tokkyo Koho JP 06320195 A2 941122 Heisei, 12 pp. (Japanese).

R.E. Paine and K.C. Thompson, "Polyelectrolyte Conditioning of Sheffield Sewage Sludge", *Wat. Sci. Tech.*, vol. 16, Vienna, pp. 473–486.

CA 104:10062b, "Control of odors from sewage sludge", Bosshard, Stephan; Ost Karl (Degussa [Schweiz] A.–G., 8040 Zurich Switz.), Gas Wasser, Abwasser 1985, 65(7), 410–13 (Ger).

CA 85:82749t, "Slime and oder elimination in process water of the paper industry", Schwab, Heinrich; Kaschke, Werner (DEGUSSA Wolfgang, Wolfgang/Nanau, Ger.)., Papier (Darmstadt) 1975 29(10A, Spec. Issue), 43–51, (Ger).

Martin Lang, "Chemical Control of Water Quality in a Tidal Basin", *Journal—Water Pollution Control Federation*, pp. 1410–1419, Sep. 1966.

Dague, *Journal—Water Pollution Control Federation*, p. 586.

*Plant Operations*, p. 301, Mar. 1981.

*Fundamental Principles of Bacteriology*, pp. 328–330.

H.A. Painter, *A Review of Literature on Inorganic Nitrogen Metabolism in Microorganisms* pp. 399–400.

Design Manual, "Odor and Corrosion Control in Sanitary Sewerage Systems and Treatment Plants", Center for Environmental Research Information, U.S. Environmental Protection Agency, Office of Research and Development, Oct. 1985, pp. 8–9.

Results of Literature Search.

*Primary Examiner*—Gary P. Straub
*Assistant Examiner*—Melanie C. Wong
*Attorney, Agent, or Firm*—Burns, Doane, Swecker & Mathis, L.L.P.

[57] ABSTRACT

A method and composition are provided for controlling odor from waste products. The composition comprises a combination of chlorite salt and nitrate salt. The method includes the step of contacting the waste products or their surrounding airspace with the composition.

10 Claims, No Drawings

METHOD AND COMPOSITION FOR ODOR CONTROL

FIELD OF THE INVENTION

The present invention relates to a method and composition for controlling odor from waste products such as organic waste produced by metabolic processes, including human and animal waste, as well as industrial wastes, effluents, sewage, and the like.

BACKGROUND OF THE INVENTION

The occurrence of volatile odorous substances is one of the problems associated with the collection and treatment of various waste materials. Domestic sewage is the largest volume source of odorous waste for which sulfides and thiols are very common odor causing constituents. Sulfides are most prominent, with hydrogen sulfide being the most objectionable odor-bearing compound in such wastes. Because of the magnitude of domestic sewage that is collected and treated and the prominence of odorous sulfidic compounds associated with this waste, the present invention is particularly directed, but not limited to the control of hydrogen sulfide and other sulfide odors in sewage. As used herein, the term "hydrogen sulfide" ($H_2S$) also includes other sulfides of divalent sulfur.

Biological activity, especially anaerobic decomposition of compounds containing sulfur, is responsible for the formation of most odorous sulfur compounds, especially $H_2S$. Sulfate ion ($SO_4^{-2}$) is the most common starting material for the generation of $H_2S$. In the absence of oxygen, sulfate-reducing bacteria (for example, *desulfovibrio desulfuricans*) will metabolize sulfate ion together with organic matter present to form $H_2S$, as represented by the following equation:

$$SO_4^{-2} + \text{organic matter} + \text{bacteria} \rightarrow H_2S + CO_2 + H_2O$$

The odor associated with $H_2S$ is similar to rotten egg odor. $H_2S$ is toxic in low concentrations. Hydrogen sulfide is also corrosive towards steel and concrete. The presence of $H_2S$ and other odor causing compounds in waste materials is a major concern for waste handling systems. One aspect of the occurrence of malodorous compounds that is often the driving force behind efforts to control odor is complaints received from citizens living in the area. Such odors are generally regarded as a public nuisance and a health hazard.

Hypochlorite (sodium or calcium), potassium permanganate, sodium nitrate, ferrous and ferric chloride, ferrous sulfate, hydrogen peroxide, chlorine, chlorine dioxide, and sodium chlorite have been widely used for the control of odor in wastes, and sewage waste in particular. For example, articles have been published and patents have been granted for the use of sodium chlorite and sodium nitrate individually to control odorous compounds. The following references mention the use of sodium chlorite by itself for odor control:

"Control of Odors from Sewage Sludge," *Gas, Wasser, Abwasser*, Vol. 65, pp. 410–413 (1985) in Chemical Abstracts 104:10062 (German);

"Polyelectrolyte Conditioning of Sheffield Sewage Sludge," *Water Science Technology*, Vol. 16, pp. 473–486 (1984) in Chemical Abstracts 102:100249;

"Slime and Odor Elimination in Process Water of the Paper Industry," *Papier*, Vol. 29, pp. 43–51 (1975) in Chemical Abstracts 85:82749 (German); and "Deodorization of Sludge for Dewatering by Controlled Adding Chlorite," Japanese Patent Publ. No. 06320195 (1994).

The following patents mention the use of nitrate by itself for odor control:

"Method of Sewage Treatment," U.S. Pat. No. 5,114,587 (May 9, 1992);

"Process for Removal of Dissolved Hydrogen Sulfide and Reduction of Sewage BOD in Sewer or Other Waste Systems," U.S. Pat. No. 4,911,843 (Mar. 27, 1990); and "Use of Alkali Metal Nitrites to Inhibit $H_2S$ Formation in Flue Gas Desulfurization System Sludges," U.S. Pat. No. 4,681,687 (Jul. 21, 1987).

In addition, patents have been issued for the use of oxidants in combination with nitrates. For example, U.S. Pat. No. 4,108,771 contains claims directed to the use of sodium chlorate and ammonium nitrate for odor control of waste materials. U.S. Pat. No. 3,966,450 contains claims directed to the use of hydrogen peroxide and the addition of nitric acid to generate nitrate salts. U.S. Pat. No. 5,200,092 contains claims directed to the use of potassium permanganate with nitrate salts for odor control.

Some of the treatments mentioned above have advantages in certain applications. However, they also suffer from various drawbacks. Some of the disadvantages of the above-mentioned treatment chemicals are listed below.

| | |
|---|---|
| Hypochlorite/chlorine | Loses strength during storage. Reacts with ammonia for additional consumption. Forms chlorinated VOCs. Generates chlorine odor with over-doses. Has no long-term effect. |
| Potassium Permanganate | Is labor intensive. Causes discoloration with over-doses. Results in precipitation of manganese. |
| Nitrates | Have no immediate or short term effect. Produce nitrogen by-products which can present treatment problems. |
| Iron Salts | Are ineffective for non-sulfide odors. Cause build-up of solids. Impure products can contain heavy metals. Can be toxic to microorganisms. Deplete dissolved oxygen and alkalinity. |
| Hydrogen Peroxide | Requires catalysis for non-sulfide odors. Causes foaming. Is not long lasting. |
| Chlorine Dioxide | Requires a generator. Generates chlorine-type odor with over-doses. Is not long lasting. |
| Sodium Chlorite | Can be costly in high doses. |

In view of the disadvantages mentioned above, there is a need in the art for a method and composition for abating odor in waste materials that is cost effective and that not only works well on all malodorous compounds, but that does not produce undesirable by-products. Accordingly, it is an object of the present invention to address this need in the art. This and other objects of the present invention will become more apparent in light of the following summary and detailed description of the invention and the appended claims.

SUMMARY OF THE INVENTION

Briefly, the present invention relates to a method and composition for controlling odor from waste products. The composition comprises a combination of chlorite salt and nitrate salt. Preferably, the composition comprises a combination of sodium chlorite and sodium nitrate. The method according to the present invention comprises the step of contacting the waste products or their surrounding airspace with the composition.

Malodorous compounds can be destroyed easily, rapidly, at a reasonable cost and continue to be controlled with the composition according to the present invention. Sodium chlorite has been found to be extremely effective in control of sulfide and other malodorous compounds found in sewage. This reaction is extremely rapid, requiring only seconds.

An additional benefit with the use of sodium chlorite is that it does not react with ammonia, so that dosing concentrations are not elevated due to ammonia demand. Sodium chlorite is generally sold in solution form (up to 50% strength), which can be easily dosed by pump action. The solution does not lose strength over time.

Sodium nitrate is added to promote residual control of sulfide formation. The sodium nitrate alters the environment, i.e., the waste, such that the sulfate-reducing bacteria stop producing $H_2S$. The concentration of nitrate salt in the solution may vary according to the residual odor control desired. The greater the amount of nitrate, the more the residual control of sulfide.

It was surprisingly and unexpectedly found that the combination of sodium chlorite and sodium nitrate provided synergism for odor control. The combination of these compounds can provide more odor control than the sum of their individual effects.

DETAILED DESCRIPTION OF THE INVENTION

The composition for controlling odor from waste products according to the present invention comprises a combination of chlorite salt and nitrate salt. As used herein, the term "controlling odor" means reducing and/or eliminating odor that is offensive to humans. Such odors are usually caused by volatile sulfides and other volatile odorous substances.

The waste products treatable with the present invention include, but are not limited to organic waste produced by metabolic processes, including human and animal waste, as well as industrial wastes, effluents, sewage, and the like. The chlorite salt employed in the composition is preferably an alkali or alkaline earth metal chlorite and is more preferably selected from the group consisting of sodium chlorite, calcium chlorite, and potassium chlorite. Likewise, the nitrate salt is preferably selected from the group consisting of sodium nitrate, calcium nitrate, and potassium nitrate.

The composition can be employed as a solid mixture. Preferably, the composition comprises from 0.5 to 99.5% by weight of the chlorite salt and from 0.5 to 99.5% by weight of the nitrate salt. In a preferred embodiment, however, the composition is employed in the form of an aqueous solution. Preferably, the solution comprises from about 0.5 to about 50% by weight of the chlorite salt, from about 0.5 to about 50% by weight of the nitrate salt, and from about 1 to about 99% by weight of water. In a particularly preferred formulation, the composition comprises about 22.5% by weight of sodium chlorite, about 10% by weight of sodium nitrate, and about 67.5% by weight of water.

A solution of sodium chlorite and sodium nitrate according to the invention can be used easily to destroy the malodorous characteristics of odor causing compounds such as sulfides found in sewage and other waste products. The solution can be pumped into the material to be treated (liquid, sludge, or solid) or sprayed onto the surface or into the airspace surrounding the material.

The sodium chlorite provides rapid control of malodorous compounds such as sulfides. The treatment concentration is directly dependent upon the amount of odor causing compounds with chlorite demand that are present in the waste.

The sodium nitrate alters the environment, i.e., the waste, so that the sulfate reducing bacteria stop producing $H_2S$. The stoppage of $H_2S$ production using nitrate is not immediate, can take from 10–24 hours, and will remain until no nitrate is present. The concentration of nitrate salt present in the treatment solution may vary depending upon the amount of residual control of malodorous compounds that is required. Nitrate is less costly than chlorite and thus lowers the cost per pound of the treatment solution. Using a combination of nitrate plus chlorite treatment of sulfide odors also has an unexpected beneficial effect. It has been surprisingly found that the treatment combination is capable of controlling sulfide odors much more effectively than the sum of the control when using either nitrate or chlorite alone.

The waste material to be treated may vary in temperature within normal operating conditions above the freezing and below the boiling point of the waste. The reaction rate may vary depending upon the temperature, which increases with increasing temperature. High temperatures in malodorous waste are generally undesirable due to an increase in volatilization of the odor causing compounds. The pH of the waste material may vary from 1 to 14.

Sodium chlorite, when added to acidic materials, will generate chlorine dioxide, which is also effective in destroying malodorous compounds. The reaction rate of sodium chlorite to chlorine dioxide increases as pH becomes lower. It is preferred, however, to avoid the use of chlorine dioxide for treating sewage. Laboratory tests have demonstrated that chlorine dioxide can cause the formation of a strong, bile-like, odor in sewage. Sodium chlorite does not form such a bile-like odor in the same application. Nonetheless, chlorine dioxide may be desired for use when sterilization is important, since it is actually a stronger oxidant than sodium chlorite. Certain other compounds when present, can cause sodium chlorite to react to form chlorine dioxide, such as acid, hypochlorite, aldehydes, and ketones.

EXAMPLES

The invention will now be described with reference to the following examples. The examples, however, are provided to illustrate the invention and are not deemed to limit any aspect thereof.

Example 1

Effect of Sodium Nitrate Addition to Odor Control of Sewage Treated with Sodium Chlorite A series of tests were conducted in the laboratory to determine the effect of adding a nitrate salt to sodium chlorite to impart residual control of malodorous compounds in sewage. Samples of sewage sludge from a municipal treatment plant in the Midwest were treated with varying concentrations of sodium chlorite with and without sodium nitrate, also of varying concentrations. The treatment chemicals were added to approximately 50 grams each of sewage sample in small plastic bottles. The bottles were capped, shaken, and stored at room temperature. After 15 minutes, the samples were physically smelled to determine the degree of odor destruction as compared to a control sample of untreated sewage. The sample bottles were then re-capped, allowed to remain at room temperature for twenty-four hours, and then re-tested for odor destruction. The results of the testing are contained in Tables 1–4 below.

In the Tables, the odor of the untreated sample was arbitrarily given a value of 100. Values of less than 100 were given to the treated samples according to the amount of decrease in odor, as a subjective observation. The odor at a value of 100 was typical of raw sewage and was extremely unpleasant. The odor at a value of 1 could be described as humus, not an unpleasant odor and typical of normal soil.

TABLE 1

Apparent Odor for Treatment with $NaClO_2$ and No $NaNO_3$

| PPM $NaClO_2$ | 274 | 547 | 1090 | 2693 |
|---|---|---|---|---|
| PPM $NaNO_3$ | 0 | 0 | 0 | 0 |
| Odor After 15 Mins. | 10 | 5 | 3 | 1 |
| Odor After 24 Hrs. | 80 | 40 | 20 | 8 |

TABLE 2

Apparent Odor for Treatment with 25:1 $NaClO_2$ to $NaNO_3$

| PPM $NaClO_2$ | 248 | 495 | 990 | 2475 |
|---|---|---|---|---|
| PPM $NaNO_3$ | 10 | 20 | 40 | 100 |
| Odor After 15 Mins. | 10 | 5 | 3 | 1 |
| Odor After 24 Hrs. | 40 | 20 | 10 | 4 |

TABLE 3

Apparent Odor for Treatment with 4.75:1 $NaClO_2$ to $NaNO_3$

| PPM $NaClO_2$ | 238 | 475 | 950 | 2375 |
|---|---|---|---|---|
| PPM $NaNO_3$ | 50 | 100 | 200 | 500 |
| Odor After 15 Mins. | 10 | 5 | 3 | 1 |
| Odor After 24 Hrs. | 20 | 10 | 5 | 2 |

TABLE 4

Apparent Odor for Treatment with 2.25:1 $NaClO_2$ to $NaNO_3$

| PPM $NaClO_2$ | 225 | 450 | 900 | 2250 |
|---|---|---|---|---|
| PPM $NaNO_3$ | 100 | 200 | 400 | 1000 |
| Odor After 15 Mins. | 10 | 5 | 3 | 1 |
| Odor After 24 Hrs. | 10 | 5 | 3 | 1 |

As can be seen from Table 1, sodium chlorite renders the sewage nearly odorless after a dose of 2693 ppm. Also as seen from Table 1, after 24 hours the odor starts to return as bacteria generate additional malodorous compounds. However, the samples that contain sodium nitrate, as in Tables 2–4, retard the formation of new odor causing compounds. The degree of residual odor control is dependent on the concentration of nitrate.

Example 2

Oxidative Effect of Sodium Nitrate on Sulfide

A series of tests were conducted in the laboratory to measure the ability of sodium nitrate to oxidize sulfide.

A sulfide water sample was prepared by dissolving 20 grams of sodium sulfide ($Na_2S$) in 1000 mLs of de-ionized water. The sample was adjusted to a pH of 7 with acetic acid and a phosphate buffer. A 10% sodium nitrate ($NaNO_3$) solution was also prepared. Sample bottles were spiked with 1.0 mL of the sulfide stock, varying amounts of the nitrate stock, and filled to a total volume of 100 mLs. This procedure allowed for a constant concentration of sulfide while varying the nitrate concentration.

The samples were analyzed for sulfide using Standard Method 4500-$S^{2-}$ F (from Standard Methods for the Examination of Water and Wastewater, $19^{th}$ ed., 1995, pp. 4–127), which is an iodometric back-titration method. This method involves adding excess iodine to the sample, which is reduced according to the concentration of sulfide present. The excess iodine is then titrated with sodium thiosulfate to determine, by difference, the amount of iodine consumed by the sulfide.

The samples were analyzed at 1, 24, 48, and 72 hours from the time of initial dosing with $NaNO_3$. The samples were stored in sealed glass bottles, in the dark, at room temperature. The normality of the iodine solution used was 0.0162 N, and the normality of the sodium thiosulfate was 0.20 N. Each titration consisted of 5 mLs of iodine solution, 5 mLs of sample, about 100 mLs of de-ionized water, potassium iodide (KI), and starch. A Hach digital titrator was used for the titrations. The results of all the tests are shown in Table 5 below.

TABLE 5

Sulfide Control by Oxidation with Sodium Nitrate

| | Sample | A | B | C | D | E | F | G | H | I |
|---|---|---|---|---|---|---|---|---|---|---|
| | $NaNO_3$ Wt. % | 0 | 0.01 | 0.05 | 0.1 | 0.2 | 0.5 | 1 | 2 | 4 |
| 1 Hr | PPM Sulfide | 158 | 165 | 163 | 165 | 164 | 163 | 162 | 161 | 162 |
| | % Control | 0 | 0 | 0 | 0 | 0 | 0 | 0 | 0 | 0 |
| 24 Hrs | PPM Sulfide | 150 | 152 | 152 | 156 | 157 | 163 | 164 | 155 | 154 |
| | % Control | 0 | 0 | 0 | 0 | 0 | 0 | 0 | 0 | 0 |
| 48 Hrs | PPM Sulfide | 149 | 152 | 162 | 150 | 154 | 161 | 158 | 154 | 157 |
| | % Control | 0 | 0 | 0 | 0 | 0 | 0 | 0 | 0 | 0 |
| 72 Hrs | PPM Sulfide | 141 | 154 | 156 | 141 | 157 | 157 | 150 | 153 | 146 |
| | % Control | 0 | 0 | 0 | 0 | 0 | 0 | 0 | 0 | 0 |

There was no observed oxidative effect of sodium nitrate on the concentration of sulfide present in any of the test samples. As seen from the results shown in Table 5, sulfide concentrations varied somewhat from the beginning of the test to the end, but in no case was there less sulfide in any of the nitrate-treated samples than in the untreated control. Therefore, it would be reasonable to conclude that any decrease in sulfide observed in tests using media other than water, such as sewage sludge, would be the result of factors other than chemical oxidation by nitrate.

Example 3

Effect of Sodium Nitrate Addition to Odor Control of Sewage Treated with Sodium Chlorite A series of laboratory tests were conducted using sewage sludge collected from a Midwestern sewage plant. The sewage sludge samples were spiked with sodium sulfide ($Na_2S$) to increase the concentration of treatable sulfide. A 3000 mL batch of sewage sludge was spiked with a liquid solution of sodium sulfide, and the batch was adjusted with sulfuric acid to a pH of 5.5 to 6.0. Plastic bottles were filled with 200 mLs of sludge each. The samples were then dosed with sodium nitrate, sodium chlorite, and the combination of the two. The samples were then capped, shaken, and centrifuged. A portion of the centrificate was titrated iodimetrically using Standard Method 4500-$S^{2-}$ F (from Standard Methods for the Examination of Water and Wastewater, $19^{th}$ ed., 1995, pp. 4–127). The samples were then re-shaken and set aside at room temperature. This analysis was repeated at 24, 48, and 72 hours.

Samples of the sulfide fortified master sludge sample were treated with sodium nitrate at concentrations of 100, 200, and 300 parts per million. A second set of master sludge samples was treated with 225, 450, and 675 parts per million sodium chlorite. A third set of master sludge samples was treated with a combination of sodium nitrate plus sodium chlorite using 100/225, 200/450, and 300/675 respective ppm sodium nitrate/ppm sodium chlorite ratios.

The results for samples treated with sodium nitrate are shown in Table 6 below. Sulfide concentrations were determined at 1, 24, 48, and 72 hours. As seen below, in general it was recorded that nitrate gave only modest control of the sulfide after one hour and also at 48 hours.

TABLE 6

Control of Sulfide Odor Versus Time with Sodium Nitrate

| Sample PPM Sulfide | A Control | B 100 PPM $NaNO_3$ | C 200 PPM $NaNO_3$ | D 300 PPM $NaNO_3$ |
| --- | --- | --- | --- | --- |
| 1 Hour | 276 ppm $S^{-2}$ | 201 | 196 | 216 |
| % Control | 0.0 | 27.2 | 29.0 | 21.7 |
| 24 Hours | 164 ppm $S^{-2}$ | 179 | 172 | 172 |
| % Control | 0.0 | 0.0 | 0.0 | 0.0 |
| 48 Hours | 169 ppm $S^{-2}$ | 139 | 152 | 159 |
| % Control | 0.0 | 17.8 | 10.1 | 5.9 |
| 72 Hours | 144 ppm $S^{-2}$ | 137 | 144 | 137 |
| % Control | 0.0 | 4.9 | 0.0 | 4.9 |

% Control = [(Initial Sulfide Conc. − Sulfide Conc. of Treated Solution) × 100] / Initial Sulfide Conc.

The results for samples treated with sodium chlorite are shown in Table 7 below. Due to the high level of sulfide in the samples, significant reduction of sulfide was not seen until the chlorite dose of 675 ppm. At this treatment level, the percent control was 66 percent after 1 hour. The percent control decreased with time, being only about 5 percent after 72 hours. Overall, chlorite was much more effective at reducing sulfide as compared to nitrate.

TABLE 7

Control of Sulfide Odor Versus Time with Sodium Chlorite

| Sample PPM Sulfide | A Control | F 225 PPM $NaClO_2$ | G 450 PPM $NaClO_2$ | H 675 PPM $NaClO_2$ |
| --- | --- | --- | --- | --- |
| 1 Hour | 276 ppm $S^{-2}$ | 188 | 199 | 94 |
| % Control | 0.0 | 31.9 | 27.9 | 65.9 |
| 24 Hours | 164 ppm $S^{-2}$ | 222 | 179 | 107 |
| % Control | 0.0 | 0.0 | 0.0 | 34.8 |
| 48 Hours | 169 ppm $S^{-2}$ | 179 | 164 | 137 |
| % Control | 0.0 | 0.0 | 0.0 | 18.9 |
| 72 Hours | 144 ppm $S^{-2}$ | 164 | 157 | 137 |
| % Control | 0.0 | 0.0 | 0.0 | 4.9 |

% Control = [(Initial Sulfide Conc. − Sulfide Conc. of Treated Solution) × 100] / Initial Sulfide Conc.

The results for samples treated with a formulation containing a combination of sodium nitrate and sodium chlorite are listed in Table 8 below. It was unexpectedly found that this combination of nitrate and chlorite was much more effective at reducing and controlling sulfide as compared to the control achieved by summing the sulfide reductions from separate nitrate and chlorite treatments. This improved control can best be described as a synergistic effect.

TABLE 8

Sulfide Control Versus Time for a Combination of Sodium Nitrate Plus Sodium Chlorite

| Sample PPM Sulfide | A Control | Combination of B + F | Combination of C + G | Combination of D + H |
| --- | --- | --- | --- | --- |
| 1 Hour | 276 ppm $S^{-2}$ | 94 | 72 | 61 |
| % Control | 0.0 | 65.9 | 73.9 | 77.9 |
| 24 Hours | 164 ppm $S^{-2}$ | 97 | 79 | 22 |
| % Control | 0.0 | 40.9 | 51.8 | 86.6 |
| 48 Hours | 169 ppm $S^{-2}$ | 89.0 | 64.0 | 29.0 |
| % Control | 0.0 | 47.3 | 62.1 | 82.8 |
| 72 Hours | 144 ppm $S^{-2}$ | 92 | 72 | 42 |
| % Control | 0.0 | 36.1 | 50.0 | 70.8 |

% Control = [(Initial Sulfide Conc. − Sulfide Conc. of Treated Solution) × 100] / Initial Sulfide Conc.

The percent synergy determined for the combination of nitrate plus chlorite treatment is shown in Table 9 below. It can be surprisingly seen that beginning at the 24 hour time period and continuing through 72 hours, the majority of the control of sulfide was due to the synergy.

TABLE 9

Percent Control of Sulfide Odor Measured as Synergistic Effect of Sodium Nitrate Plus Sodium Chlorite Formulation

| % Synergistic Control Hours | Combination of B + F | Combination of C + G | Combination of D + H |
| --- | --- | --- | --- |
| 1 | 10.3% | 23.1% | 0.0% |
| 24 | 100.0 | 100.0 | 59.8 |
| 48 | 62.4 | 78.9 | 70.0 |
| 72 | 86.4 | 100.0 | 86.2 |

Percent Synergist Effect = {[Sulfide after Combination Treatment − (Sulfide after Nitrate Treatment + Sulfide after Chlorite Treatment)] × 100} / Sulfide after Combination Treatment A convenient method for quantifying the synergistic effect was calculated as follows:

Percent Synergy={[c−(a+b)]×100}/c where
- a=Percent Control of Sulfide after Nitrate Treatment;
- b=Percent Control of Sulfide after Chlorite Treatment; and
- c=Percent Control of Sulfide after Combination Treatment.

As an example of the synergistic effect, the advantage of the combined formulation is demonstrated more fully in Table 10 below. This Table shows the data for the experiment using the highest chemical doses of the combination formulation tested, i.e., 300 ppm sodium nitrate plus 675 ppm sodium chlorite.

TABLE 10

Percent Control of Sulfide Versus Time and Comparison of Additive and Combination Effects of Treatment of Sulfide with Nitrate and Chlorite

| Percent Control Hours | a NaNO$_3$ 300 ppm | b NaClO$_2$ 675 ppm | (a + b) Additive Effect 300 ppm NaNO$_3$ 675 ppm NaClO$_2$ | c Combination Effect 300 ppm NaNO$_3$ 675 ppm NaClO$_2$ | Combination Effect Percent Synergistic Control |
|---|---|---|---|---|---|
| 1 | 21.7% | 65.9% | 87.6% | 77.9% | 0.0% |
| 24 | 0.0 | 34.8 | 34.8 | 86.6 | 59.8 |
| 48 | 5.9 | 18.9 | 24.8 | 82.8 | 70.0 |
| 72 | 4.9 | 4.9 | 9.8 | 70.8 | 86.2 |

As seen in Table 10 above, exceptional control of sulfide was achieved with the combination of nitrate plus chlorite as compared to the additive effects of nitrate and chlorite. The combination is especially effective beginning at some period after one hour through 72 hours and beyond. At 72 hours, only 10 percent control of sulfide was achieved with the additive effects of separate nitrate and chlorite treatment as compared to the 70.8 percent control with the combination of nitrate plus chlorite treatment. Therefore, the synergistic effect accounted for 86 percent of the control, i.e., $\{[70.8-(4.9+4.9)]\times 100\}/70.8=86.2\%$.

While the invention has been described with reference to particular preferred embodiments and examples, it is to be understood that variations and modifications may be resorted to as will be apparent to those skilled in the art. Such variations and modifications are to be considered within the purview and the scope of the claims appended hereto.

What is claimed is:

1. A method for controlling odor from waste products, the method comprising the step of:
   contacting the waste products or their surrounding airspace with a composition comprising a combination of chlorite salt and nitrate salt in a weight ratio of about 2.25:1 chlorite salt to nitrate salt.

2. The method according to claim 1, wherein the chlorite salt is an alkali or alkaline earth metal chlorite.

3. The method according to claim 2, wherein the chlorite salt is selected from the group consisting of sodium chlorite, calcium chlorite, and potassium chlorite.

4. The method according to claim 1, wherein the nitrate salt is selected from the group consisting of sodium nitrate, calcium nitrate, and potassium nitrate.

5. The method according to claim 1, wherein the composition comprises from 0.5 to 99.5% by weight of the chlorite salt.

6. The method according to claim 1, wherein the composition is in the form of an aqueous solution.

7. The method according to claim 6, wherein the composition comprises from about 0.5 to about 50% by weight of the chlorite salt, and from about 1 to about 99% by weight of water.

8. The method according to claim 7, wherein the chlorite salt is sodium chlorite and the nitrate salt is sodium nitrate.

9. The method according to claim 8, wherein the composition comprises about 22.5% by weight of sodium chlorite, about 10% by weight of sodium nitrate, and about 67.5% by weight of water.

10. The method according to claim 1, wherein the composition further comprises an acid, hypochlorite, aldehyde, or ketone.

* * * * *